(12) United States Patent
Propp

(10) Patent No.: US 7,294,752 B1
(45) Date of Patent: Nov. 13, 2007

(54) WINDOW DRESSING HAVING INTEGRAL ANCHOR

(75) Inventor: Donald J. Propp, Dewitt, MI (US)

(73) Assignee: Tri-State Hospital Supply Corporation, Howell, MI (US)

( * ) Notice: Subject to any disclaimer, the term of this patent is extended or adjusted under 35 U.S.C. 154(b) by 9 days.

(21) Appl. No.: 11/475,478

(22) Filed: Jun. 27, 2006

(51) Int. Cl.
*A61F 13/00* (2006.01)
*A61M 5/32* (2006.01)

(52) U.S. Cl. ............................ 602/58; 602/42; 602/43; 602/52; 602/54; 604/180

(58) Field of Classification Search ............ 602/41–43, 602/52, 54, 58; 604/179, 180; D24/189
See application file for complete search history.

(56) References Cited

U.S. PATENT DOCUMENTS 5,885,254 A * 3/1999 Matyas ....................... 604/180
6,124,520 A * 9/2000 Roberts ....................... 602/54
6,124,521 A * 9/2000 Roberts ....................... 602/54
6,841,715 B2 * 1/2005 Roberts ....................... 602/54

* cited by examiner

*Primary Examiner*—Kim M. Lewis
(74) *Attorney, Agent, or Firm*—Fildes & Outland, P.C.

(57) ABSTRACT

A window dressing with an integral anchor includes a fabric layer having juxtaposed insertion site viewing and anchor member portions. The fabric layer has an adhesive side and an opposite non-adhesive side. The insertion site viewing portion is defined by an opening in the fabric layer. A transparent film layer having an adhesive skin-adhering side and an opposite non-adhesive side is adhered to the fabric layer adhesive side and closes the opening in the fabric layer. The anchor member portion includes a reinforcing structure disposed on the fabric layer. The reinforcing structure has an adhesive side and an opposite non-adhesive side. The non-adhesive side is adhered to the fabric layer adhesive side. A first removable securement device may be removably connected to the anchor member portion opposite the insertion site viewing portion, and a second removable securement device may be removably connected to the first removable securement device.

20 Claims, 4 Drawing Sheets

WINDOW DRESSING HAVING INTEGRAL ANCHOR

TECHNICAL FIELD

This invention relates to medical dressings, and more particularly to self-adherent window dressings for the viewing, protection, and securement of PICC, CVC, IJ, subclavian, femoral, and implant port catheters about an insertion site.

BACKGROUND OF THE INVENTION

It is known in the art relating to medical dressings for the protection and securement of catheters to apply a dressing to a patient's skin to cover a catheter insertion site at which the catheter punctures a patient's skin. It is also common for medical clinicians (i.e., doctors, nurses, and other medical personnel) to alternatively or additionally apply strips of medical grade tape to attempt to secure the catheter or associated medical tubing. Another conventional clinical practice is to suture a catheter hub to a patient's skin to roughly secure the catheter to the patient. Further still, a variety of catheter and medical tubing securement devices are available for use in the medical field. These securement devices, however, are often bulky and cumbersome, hard to dress with a dressing, and may have costly and complex mechanical features.

Although a wide variety of medical dressings and catheter and tubing securement devices are commercially available, individual clinicians tend to prefer to use one or a few dressings and securement devices for multiple and often unintended applications. Therefore, the dressing or securement device used is often too big or too small for the insertion site and surrounding bodily contours, or may simply have a design structure that is functionally incompatible with the application. This self-customization by clinicians therefore leads to poor catheter securement and protection.

Furthermore, it is also known in the medical field that poorly dressed and poorly secured catheters and associated tubing are likely to undesirably lead to irritation of the insertion site, necessitating movement of the catheter to a new insertion site. Even worse, poorly secured catheters are susceptible to accidental dislodgement from the insertion site. For example, medical tubing connected to indwelling catheters, infusion needles and the like is often subjected to inadvertent but significant pulling forces either caused directly by patient movement or by snagging of the tubing on other objects. These pulling forces peel the medical tape or dressing securing the catheter and/or tubing off the patient's skin. This exposes the catheter, infusion needle, etc. to movement inward or outward, increasing the likelihood that the catheter, infusion needle, etc. will fail and have to be replaced and inserted into a new insertion site. Also, this may weaken the adhesion between the dressing and the patient's skin, potentially exposing the insertion site to harmful bacteria.

SUMMARY OF THE INVENTION

The present invention provides a multi-use, "universal" medical dressing having an integral anchor for use in protecting an array of catheter insertion sites, such as PICC sites, CVC sites, IJ sites, subclavian sites, femoral sites, and implant port infusion needle sites. The present medical dressing is capable of securing a variety of catheters, infusion needles, and associated hubs, connectors, ports, and tubing. The present medical dressing may also provide at least one integral, detachable tubing anchoring strip having an integral anchoring member for anchoring catheter or infusion needle associated tubing upstream of the insertion site and spacedly from the dressing.

More particularly, a window dressing in accordance with the invention includes a fabric layer having juxtaposed insertion site viewing and anchor member portions. The fabric layer has an adhesive side and an opposite non-adhesive side. The insertion site viewing portion is defined by an opening in the fabric layer. A transparent film layer having an adhesive skin-adhering side and an opposite non-adhesive side is adhered to the fabric layer adhesive side and closes the opening in the fabric layer. The anchor member portion includes a reinforcing structure disposed under the fabric layer. The reinforcing structure has an adhesive side and an opposite non-adhesive side. The non-adhesive side is adhered to the fabric layer adhesive side.

In a specific embodiment, the reinforcing structure may include a central body and a plurality of spaced ribs extending outwardly from the central body. The reinforcing structure may also include an opening in the central body. The reinforcing structure may further include a generally circular portion at a terminal end of at least one of the ribs. The reinforcing structure may be generally symmetric about one of its axes. The central body of the reinforcing structure may be generally D-shaped.

The window dressing may also include an opening in the anchor member portion of the fabric layer that is generally surrounded by the reinforcing structure. The opening in the anchor member portion may be smaller in area than the opening in the insertion site viewing portion. A pad member adhered to the film layer adhesive side may generally circumscribe the viewing portion opening.

The window dressing may further include a pair of side perforation lines. Each side perforation line extends inwardly from an edge of the fabric layer and is generally perpendicular to the fabric layer edge. A landmark notch may be disposed along the fabric layer edge at an end of each side perforation line. The window dressing may also include a pair of removal perforation lines extending inwardly from an edge of the fabric layer and meeting at a point within the edge. A landmark notch may be disposed along the fabric layer edge at an end of each removal perforation line. A center cut line may extend inwardly from an edge of the fabric layer to the reinforcing structure.

Optionally, the window dressing may include a first removable securement device including a fabric layer having an adhesive side and an opposite non-adhesive side and a reinforcing structure having an adhesive side and an opposite non-adhesive side. The reinforcing structure non-adhesive side is adhered to the fabric layer adhesive side. A transparent film layer having an adhesive skin-adhering side and an opposite non-adhesive side is adhered to the fabric layer adhesive side. The first removable securement device is removably connected to the anchor member portion opposite the insertion site viewing portion by a plurality of frangible lands.

The window dressing may optionally further include a second removable securement device including a fabric layer having an adhesive side and an opposite non-adhesive side and a reinforcing structure having an adhesive side and an opposite non-adhesive side. The reinforcing structure non-adhesive side is adhered to the fabric layer adhesive side. A transparent film layer having an adhesive skin-adhering side and an opposite non-adhesive side is adhered to the fabric layer adhesive side. The second removable securement device is removably connected to the first removable securement device by a plurality of frangible lands.

The reinforcing structure of the first and second removable securement devices may each include a central body and a pair of opposed arms extending from the central body. The reinforcing structure of the first and second removable securement devices may also each include a plurality of perforation lines in the central body.

The dressing may be symmetrical about a longitudinal axis.

These and other features and advantages of the invention will be more fully understood from the following detailed description of the invention taken together with the accompanying drawings.

DETAILED DESCRIPTION OF THE INVENTION

Figure 1:
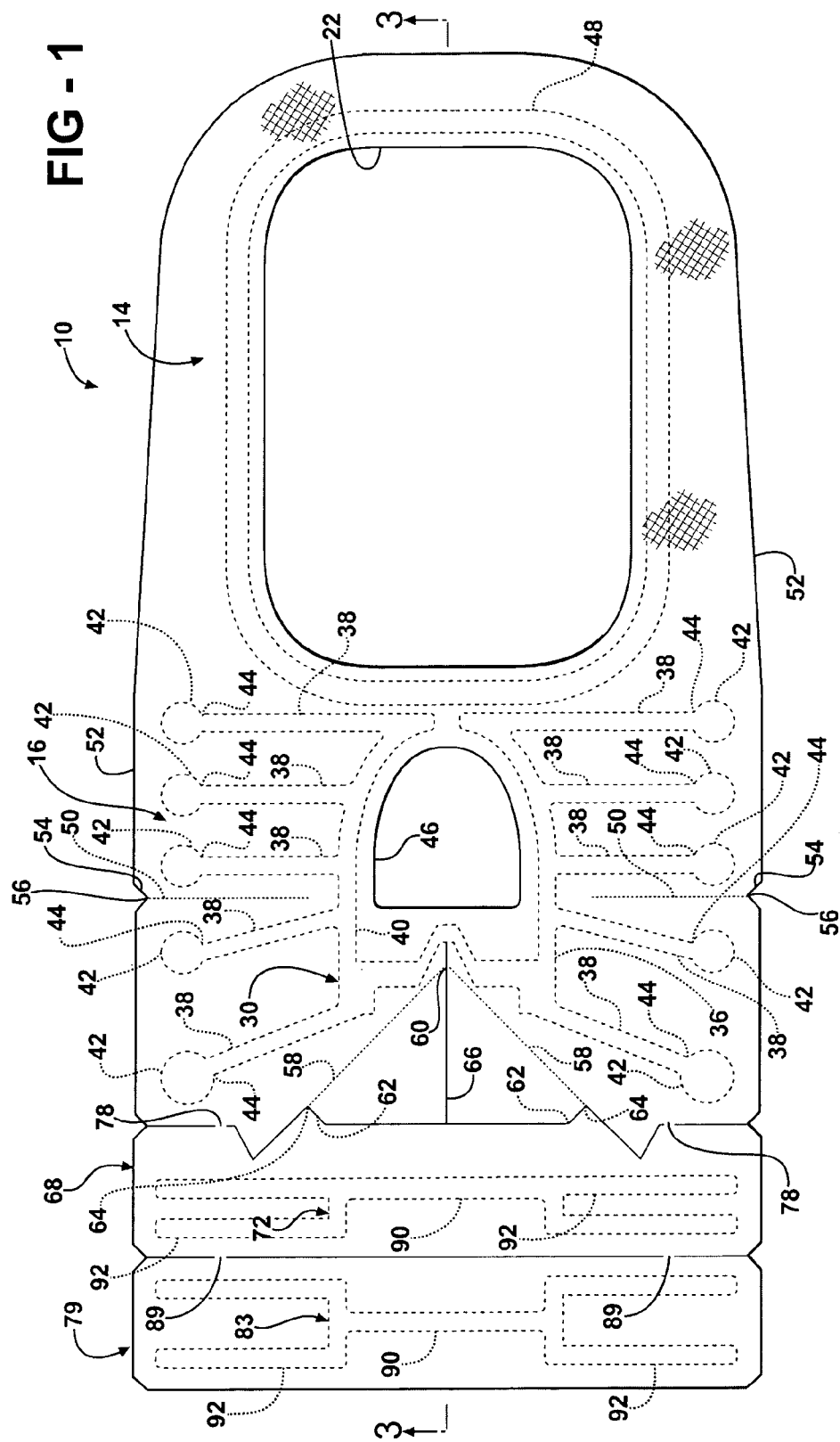
FIG. 1 is a plan view of a window dressing with integral anchor in accordance with the present invention.

Referring now to the drawings in detail, numeral 10 generally indicates a window dressing with an integral anchor member that may be used to view, protect, and secure a catheter inserted into a catheter insertion site such as a PICC ("peripherally inserted central venous catheter") insertion site, a jugular insertion site, a subclavian insertion site, a femoral insertion site, or an implanted port insertion site. The medical dressing 10 is capable of securing a variety of sizes, shapes, and types of catheters (single lumen, double lumen, triple, and quad lumen), infusion needles, and associated hubs, ports, and tubing. The window dressing 10 provides protection against microbial ingress and site or patient systemic infection, and secures the catheter and associated hubs, ports, and tubing so that forces acting on the tubing and catheter do not peel the dressing from a patient's skin or cause the catheter to become dislodged. The window dressing 10 may also include one or more removable securement devices that are anchoring strips for anchoring catheter or infusion needle associated tubing to a patient's body or other object to further prevent dislodgement of an inserted catheter. The removable securement devices also may be used to anchor a tubing exit end of the dressing 10 when the dressing is applied to a patient.

Figure 2:
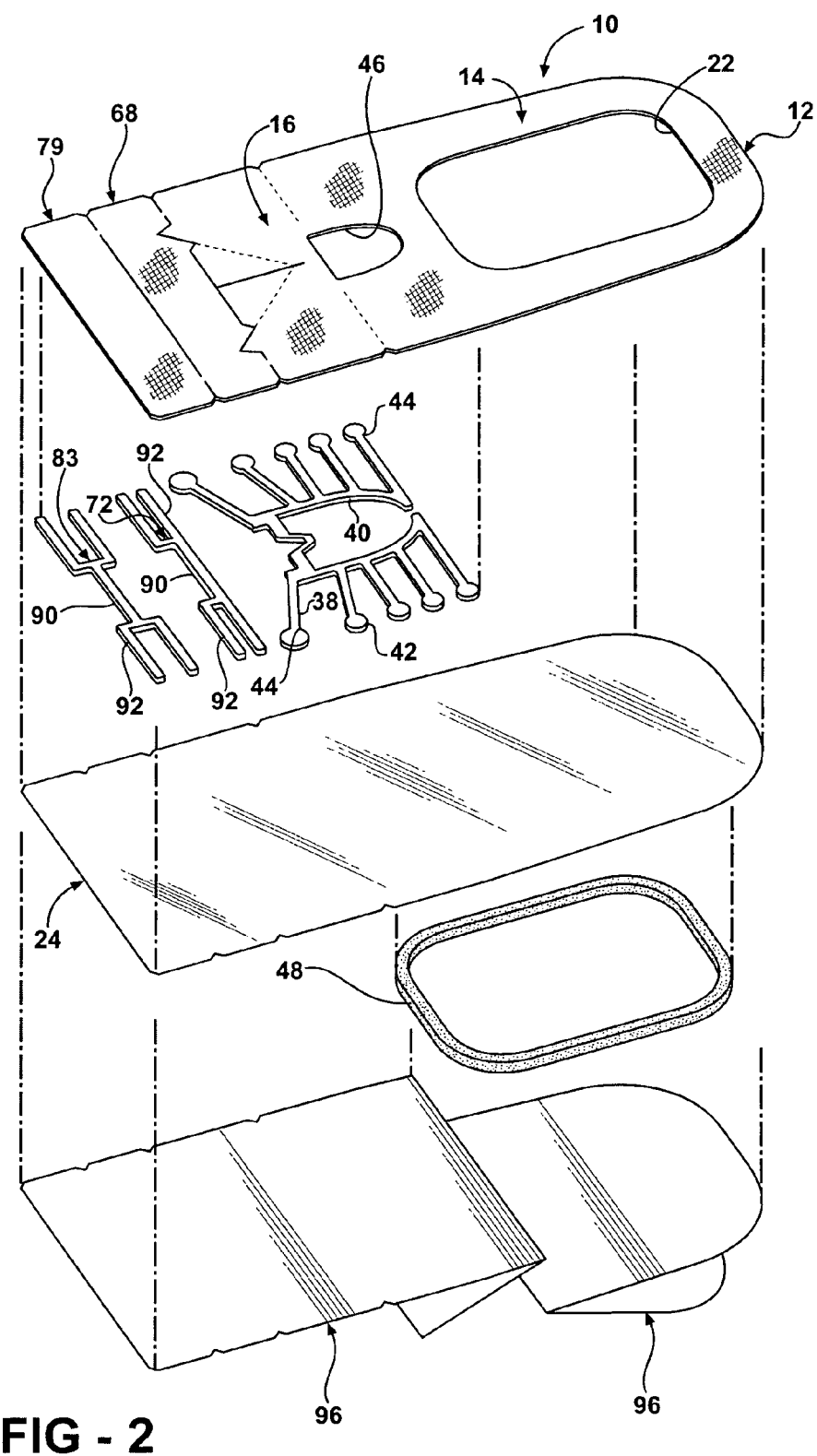
FIG. 2 is an exploded view of the window dressing of FIG. 1.
Figure 3:
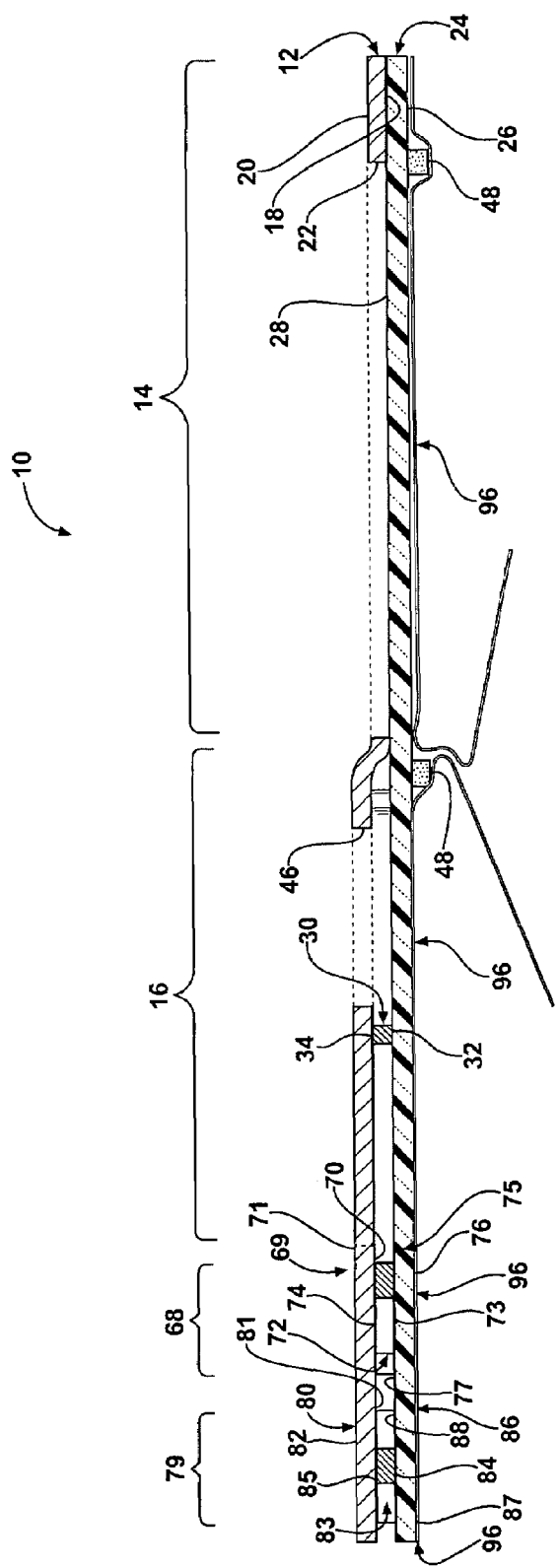
FIG. 3 is a cross-sectional view of the window dressing taken along the line 3-3 in FIG. 1.

With reference to FIGS. 1 through 3, the window dressing 10 includes a fabric layer 12 having an insertion site viewing portion 14 and an anchor member portion 16 that are juxtaposed. The fabric layer 12 may be a woven or non-woven material. The fabric layer 12 has an adhesive side 18 and an opposite non-adhesive side 20. The adhesive side 18 may be coated with any suitable medical grade adhesive. The insertion site viewing portion 14 is defined by an opening 22 in the fabric layer 12. A transparent film layer 24 having an adhesive skin-adhering side 26 and an opposite non-adhesive side 28 is adhered by its non-adhesive side 28 to the fabric layer adhesive side 18. The transparent film layer 24 closes the opening 22 in the fabric layer 12. The transparent film layer 24 may be a polyurethane film coated on one side with any suitable medical grade adhesive. The anchor member portion 16 includes a reinforcing structure 30 disposed on the fabric layer 12. The reinforcing structure 30 has an adhesive side 32 and an opposite non-adhesive side 34. The non-adhesive side 34 is adhered to the fabric layer adhesive side 18. The reinforcing structure 30 may be made of a polypropylene net material or another similar material having rigidizing and force spreading properties as discussed below.

The reinforcing structure 30 may be any shape that has multiple axes such as an X-shape, another similar hub-and-spoke shape, or a backbone and rib shape. In one specific embodiment, the reinforcing structure 30 may include a central body 36 and a plurality of spaced ribs 38 extending outwardly from the central body 36. As shown in FIG. 1, the reinforcing structure 30 may have 10 ribs, although fewer or more ribs are within the scope of the invention. The reinforcing structure 30 may also include an opening 40 in the central body 36. The opening 40 allows for the reinforcing structure 30 to surround a catheter hub without lying directly on top of the hub. The reinforcing structure 30 may further include a generally circular portion 42 at a terminal end 44 of at least one of the ribs 38. The circular portion(s) 42 generally have a radius that is larger than the width of the ribs 38 and have a curved outer edge. The circular portion(s) 42 add strength to the ends 44 of the ribs by providing more surface area at the rib ends 44, which increases the surface area for dispersing pulling forces as described in greater detail below. The reinforcing structure 30 may be generally symmetric about one of its axes. The central body 36 of the reinforcing structure 30 may be generally D-shaped, shield-shaped, or truncated-elliptical shaped, or oval shaped.

The reinforcing structure 30 strengthens the dressing 10 by making it less floppy for easier application to a patient's skin. More importantly, when the dressing 10 is applied to a patient's skin, the reinforcing structure spreads the external forces that are exerted on the dressing by the tubing over a large surface area, greatly increasing the dressing's resistance to premature separation from the patient's skin. Likewise, the reinforcing structure 30 increases the amount of force necessary to separate the dressing 10 from a patient's skin. External forces are not as localized which is the typical reason small forces are able to commence peeling of a dressing by stretching the fabric and film in a local area which then propagates onward. Commonly, external forces are exerted on the dressing 10 by pulling, snagging, or tugging on the ports, pigtails, fittings, and/or medical tubing that are connected to the catheter hub. For example, movement of the medical tubing may be caused by the patient moving, by snagging of the tubing on other neighboring objects, by a clinician moving the tubing or the patient, or any combination of the above. The reinforcing structure 30 also prevents premature separation of the dressing 10 from a patient's skin by preventing the dressing from stretching when the dressing is tugged on as described above, for example, when the tubing connected to the catheter hub is pulled on. Stretching of a dressing locally can ultimately lead to a dressing separating fully from a patient's skin. In sum, the reinforcing structure 30 increases the withstand of the dressing 10 and greatly increases the amount of multi-directional pulling force that is necessary to cause the dressing to separate from a patient's skin.

The window dressing 10 may also include an opening 46 in the anchor member portion 16 of the fabric layer 12 that is generally surrounded by the reinforcing structure 30. Specifically, the opening 46 may be surrounded by the central body 36 of the reinforcing structure 30 and may be generally similar in area to the opening 40 in the central body 36. The opening 46 in the anchor member portion 16 may be smaller in area than the opening 22 in the insertion site viewing portion 14. The transparent film layer 24 closes the opening 46 to form a window for viewing therethrough. The anchor member portion opening 46 allows for the viewing of the catheter hub so that a clinician may read the manufacturer part number or gage printed on the hub. Further, the opening 46 allows for viewing of the skin so that a clinician can ascertain whether any irritation, redness, or maceration is occurring under or at the perimeter of the catheter hub. Moreover, if the catheter hub is also secured to the patient's skin by sutures, the opening 46 allows for viewing of the sutures to ascertain whether the sutures remain intact. Even more, the transparent film layer 24, which is very elastic, closing the opening 46 rises up and stretches over a catheter hub when the dressing 10 is applied to a patient. This causes a pocket to be formed for the hub and traps the central body 36 of the reinforcing structure 30 behind the hub, further securing the hub and preventing movement of the hub when the hub is subjected to pulling forces exerted by the tubing connected to the hub. At extreme, but not atypical, tug forces on the pigtail tubing, the hub may try to slide back, but the back end of reinforcement structure 36, near point 60, hits the back of the hub, effectively "snagging it," then requiring all of the net structure to come free before any further hub motion can occur. A very high force is needed to do this. This very high security is created 50 to 100% more than current devices.

A pad member 48 may be adhered to the film layer adhesive side 26 and may generally circumscribe the viewing portion opening 22. The pad member 48 may be relatively thin and may have a low absorbent capacity, such as a capacity of approximately 2-3 cc. The pad member 48, however, is capable of preventing the egress of certain amounts of exudate and other liquids from beyond the viewing portion 14. It is not necessary for the pad 48 to have a large absorbent capacity for most typical catheters and insertion sites. It is likely that in practice the dressing 10 would be replaced before or at the time that a small amount of exudate has been absorbed by the pad 48.

The window dressing 10 may further include a pair of side perforation lines 50. Each side perforation line 50 extends inwardly from an edge 52 of the fabric layer 12 and is generally perpendicular to the fabric layer edge 52. A landmark notch 54 may be disposed along the fabric layer edge 52 at an end 56 of each side perforation line 50. The side perforation lines 50 may be separated and opened prior to application of the dressing 10 in order to more effectively anchor tubing extending from sideported catheter hubs such as a sideported CVC. Each of the pair of side perforation lines 50 are disposed symmetrically on opposite sides of the dressing 10, allowing the dressing to accommodate either left-handed or right-handed sideports. In a specific embodiment, the side perforation lines 50 may extend between two of the spaced ribs 38. The landmark notches 54 aid a clinician or other user in locating the ends 56 of the side perforation lines 50 when it is necessary or desirable to tear one of the side perforation lines.

The window dressing 10 may also include a pair of removal perforation lines 58 extending inwardly from the edge 52 of the fabric layer 12 and meeting at a point 60 within the edge 52. A landmark notch 62 may be disposed along the fabric layer edge 52 at an end 64 of each removal perforation line 58. A tubing exit center cut line 66 may extend inwardly from the edge 52 of the fabric layer 12 to the reinforcing structure 30. The center cut line 66 allows for overlapping of the rear portion of the dressing 10 to seal around a catheter hub and associated tubing extending from the hub. The removal perforation lines 58 may be torn when it is desired to remove the dressing from a patient's skin. Tearing of the removal perforation lines 58 allows the dressing 10 to be freed from under the tubing extending from the catheter hub, facilitating detachment of the dressing from a patient's skin. The landmark notches 62 help a clinician or other user of the dressing 10 locate the ends 64 of the removal perforation lines 58 when it is necessary to tear the removal perforation lines.

Optionally, the window dressing 10 may include a first removable securement device 68 including a fabric layer 69 having an adhesive side 70 and an opposite non-adhesive side 71, and a reinforcing structure 72 having an adhesive side 73 and an opposite non-adhesive side 74. The reinforcing structure non-adhesive side 74 is adhered to the fabric layer adhesive side 70. A transparent film layer 75 having an adhesive skin-adhering side 76 and an opposite non-adhesive side 77 is adhered to the fabric layer adhesive side 70 by its non-adhesive side 77. The first removable securement device 68 is removably connected to the anchor member portion 16 opposite the insertion site viewing portion 14 by a plurality of frangible lands 78.

The window dressing 10 may optionally further include a second removable securement device 79 including a fabric layer 80 having an adhesive side 81 and an opposite non-adhesive side 82, and a reinforcing structure 83 having an adhesive side 84 and an opposite non-adhesive side 85. The reinforcing structure non-adhesive side 85 is adhered to the fabric layer adhesive side 81. A transparent film layer 86 having an adhesive skin-adhering side 87 and an opposite non-adhesive side 88 is adhered to the fabric layer adhesive side 81 by its non-adhesive side 88. The second removable securement device 79 is removably connected to the first removable securement device 68 by a plurality of frangible lands 89.

The reinforcing structures 72, 83 of the first and second removable securement devices 68, 79, respectively, may each include a central body 90 and a pair of opposed arms 92 extending from the central body 90. The opposed arms 92 may be fork-like structures that each have two prongs, although arms having more than two prongs are within the scope of the invention. Alternatively, the arms 92 may have only one prong extending laterally from the body 90 and may have T-shaped ends. The reinforcing structures 72, 83 may be made of the same polypropylene net material as the dressing reinforcing structure 30, or may be made of another similar material. This pronged structure allows very fluid tight close up around/under pigtails exiting from under the dressing while prongs 92 allow flat layment away from the tubing exit point from the dressing.

The first and second removable securement device 68, 79, if present, should be removed from the dressing 10 prior to the application of the dressing 10 to a patient's skin. The frangible lands 78 between the first removable securement device 68 and the anchor member portion 16 of the dressing 10 may be torn to separate the first and second removable securement devices 68, 79 from the dressing. The frangible lands 89 between the first removable securement device 68 and the second removable securement device 79 may then be torn to separate the first and second removable securement devices from each other. Alternatively, the second removable securement device 79 may be removed from the first removable securement device 68 prior to removing the first removable securement device 68 from the anchor member portion 16 of the dressing 10. After application of the dressing 10 to a patient's skin, one or both of the first and second removable securement devices 68, 79 may be applied over the end of the anchor member portion 16 of the dressing about the center cut line 66 where tubing attached to a catheter hub exits from underneath the dressing. The securement device(s) should also be disposed underneath the tubing. It is also possible to interleave catheter lumen pigtails in between layers of the dressing and the two securement devices 68, 79. This is especially helpful when the catheter hub is large or the lumen have large outside diameters. In this arrangement, the securement device(s) reinforce the exit end of the dressing 10 and further prevent pulling forces on the tubing from tearing the dressing from the patient's skin. The securement devices also aid in sealing/closing any opening left in the dressing where the tubing exits from underneath the dressing. The removable securement devices 68, 79 may also be applied to the patient's skin or another object to anchor catheter associated medical tubing upstream of the catheter and dressing 10. The first and second removable securement devices 68, 79 are conveniently supplied with the dressing 10 and are strong tubing anchors that can be used in combination with the dressing in lieu of strips of adhesive medical tape. A 360° wrap of the device around a tubing greatly increases slide withstand of tubing through the securement.

The first and second removable securement devices 68, 79 may be integrally formed by rotary conversion processes with the anchor member portion 16 and insertion site viewing portion 14. In other words, the fabric layer 12 of the insertion site viewing portion 14 and anchor member portion 16, the fabric layer 69 of the first removable securement device 68, and the fabric layer 80 of the second removable securement device 79 may be continuous with each other and formed from a single piece of material. Likewise, the transparent film layer 24 of the insertion site viewing portion 14 and anchor member portion 16, the transparent film layer 75 of the first removable securement device 68, and the transparent film layer 86 of the second removable securement device 79 may be continuous with each other and formed from a single piece of material. Similarly, the frangible lands 78 may be defined by the fabric layer and film layer at the intersection of the anchor member portion 16 and the first removable securement device 68, and the frangible lands 89 may be defined by the fabric layer and film layer at the intersection of the first removable securement device 68 and second removable securement device 79. The dressing 10 also may be made by a rotary conversion machine for high efficiency of economy.

A release liner 96 may cover the film layer adhesive side 26 of the insertion site viewing portion 14 and anchor member portion 16, as well as the film layer adhesive side 76 of the first removable securement device 68 and the film layer adhesive side 87 of the second removable securement device 79. The release liner 96 prevents the adhesive on the film layers 24, 75, 86 from inadvertently and prematurely sticking to an object prior to application. In a specific embodiment, the release liner 96 may be a two piece, V-fold butterfly type release liner. In this embodiment, each piece of the release liner 96 covers a portion of the dressing 10. Each piece of the release liner 96 also includes a tab portion folded on top of itself. The tab portions may be gripped by a clinician for easy removal of the release liner 96 prior to application of the dressing 10. Further, portions of the release liner covering the film layer adhesive sides 76, 87 of the removable securement devices 68, 79 may have a sinuous perforation cut traversing the width of the securement devices that facilitates removal of the release liner from the film layer adhesive sides, after they are removed from the anchor member portion 16 and the frangible lands 78, 89 are detached.

For packaging and storage prior to use, the dressing 10 may be folded once or alternatively may be folded twice. For example, the dressing 10 may be folded first along an imaginary line that generally separates the anchor member portion 16 from the first removable securement device 68. This folds the dressing 10 so that it is generally two-thirds of its total length. The dressing 10 may then be folded along an imaginary line that generally separates the insertion site viewing portion 14 from the anchor member portion 16. In this configuration, the dressing 10 is generally folded in thirds. Folding the dressing 10 allows the dressing to more easily fit in a medical procedure kit or catheter accessory kit. It also allows the dressing 10 to be slipped into a folded piece of release liner that functions as a release liner "wallet." The "wallet" protects the adhesive along the folded edge(s) from arbitrarily sticking to another object.

The dressing 10 may be symmetrical about a longitudinal axis that extends through the insertion site viewing portion 14, anchor member portion 16, first removable securement device 68, and second removable securement device 79, and splits the dressing 10 into equivalent left-hand and right-hand sides. The symmetry of the dressing 10 allows the dressing to be used on either the left-hand or right-hand side of a patient's body.

In a specific embodiment, the insertion site viewing portion 14 and anchor member portion 16 may have a total length of approximately 6 inches and a width of approximately 3.5 inches. The opening 22 in the insertion site viewing portion 14 may be generally 3 inches long and 2.1 inches wide. The pad member 48 surrounding the opening 22 may be approximately 0.150 inches wide. Each rib may be approximately 0.1 inch in width and between approximately 1.0 inch and 1.3 inches in length. The first and second removable securement devices 68, 79 may each be 3.5 inches in length and 0.75 inches in width. The central body 90 of the reinforcing structures 72, 83 may be approximately 0.8 inches in length and 0.55 inches in width, and the opposed arms 92 may each be approximately 1.1 inches in length. The dressing 10 may be folded twice to resulting dimensions of approximately 4 inches by 3.5 inches. It should be understood, however, that the dressing 10 may be made larger or smaller than these dimensions by a scale factor, or may have dimensions that are not just scaled and that otherwise vary from this specific embodiment. As described above, other geometries of the reinforcement structure may deviate greatly from this specific embodiment and will accomplish similar tug withstand performance.

To apply the dressing 10 to an insertion site on a patient, the dressing 10 is first unfolded. Next, the first and second removable securement devices 68, 79 are removed from the anchor member portion 16 by tearing the frangible lands 78. If the catheter inserted into the patient includes a sideport, the appropriate side perforation line 50 may also be torn prior to application. Next, the portion of the release liner 96 covering the insertion site viewing portion 14 of the dressing 10 is removed to expose the adhesive on the transparent film layer 24. The insertion site viewing portion 14 is centered about the catheter insertion site on the patient so that the insertion site is generally in the center of the opening 22.

This allows the insertion site to be easily viewed through the opening 22. At the same time, the catheter hub is blindly centered approximately underneath the opening 40 in the central body 36 of the reinforcing structure 30 so that the hub may be viewed through the opening 46 in the anchor member portion 16 of the dressing 10. The opening 40 must be blindly aligned with the catheter hub because at this step the release liner still covers the opening 40. The properly aligned insertion site viewing portion 14 is then adhered to the patient's skin.

Next, the portion of the release liner 96 covering the anchor member portion 16 is removed by grasping the tab of the release liner and pulling away from the insertion site viewing portion 14. The tubing connected to the hub is generally arranged to exit from underneath the dressing 10, and the ends of the dressing 10 adjacent the center cut line 66 may be overlapped slightly underneath the tubing to seal the dressing 10 around the tubing. Any tubing connected to a sideport is secured by overlapping the ends of the torn side perforation line 50 underneath the sideport tubing.

If one or both of the first and second removable securement devices 68, 79 are needed, the release liner 96 may be removed from the first and second removable securement devices 6.8, 79, by bending to expose the "crack and peel" release liner on each. One of the first and second removable securement devices 68, 79 then may be placed over the end of the dressing 10 where the tubing exits from underneath the dressing adjacent point 60 to further secure the dressing. For example, the first removable securement device 68 may be snugged underneath the tubing and up against the point at which the tubing exits from underneath the dressing to close any opening in the dressing between the tubing and the folded ends of the dressing, to attempt to make the dressing "shower-proof," i.e. to completely seal the dressing. Alternatively, the first and/or second removable securement devices may be interleaved between the dressing and each catheter lumen to more tightly close the opening in the dressing around the folded over portions.

One or both of the first and second removable securement devices 68, 79 may also be placed over or wrapped fully 360° around the tubing and adhered to the patient's skin or another object at a location spaced from the dressing 10 and upstream of the catheter. The first and second removable securement devices 68, 79 further prevent tugging or pulling forces on the tubing from disturbing the dressing 10 and likewise the catheter and catheter hub located about the insertion site. They may bend slightly off the main dressing in order to facilitate finding the ends of the securement devices for removal.

To remove the dressing 10, first the end of each securement device is pulled up and lifted from slit 66, then one or both of the removal perforation lines 58 is torn to release the dressing from underneath the tubing exiting from underneath the dressing about the center cut line 66. The dressing 10 can then be removed from the patient's skin by a single pull motion from the "back" of the dressing adjacent the anchor member portion 16 towards the insertion site viewing portion 14.

Figure 4:
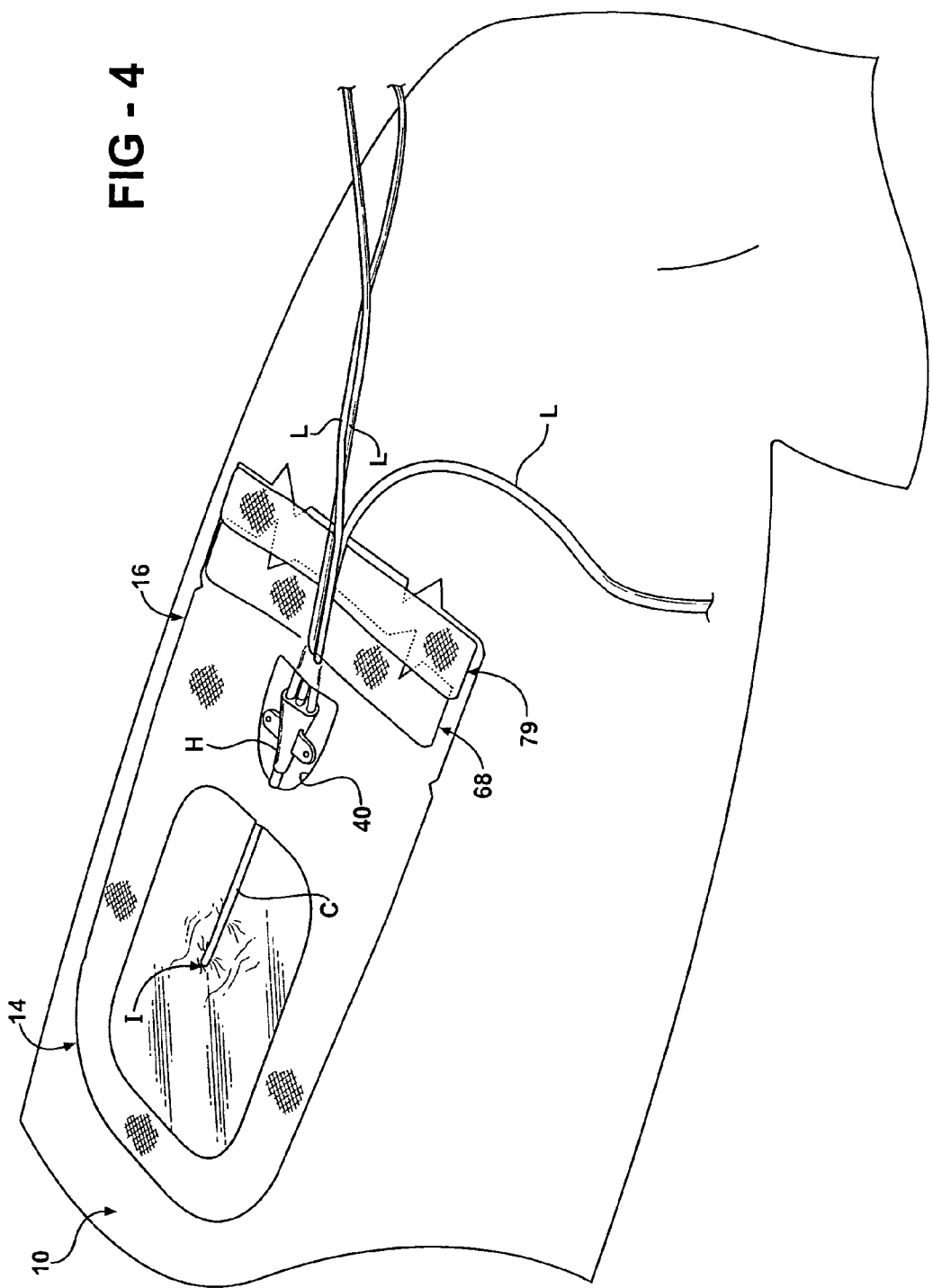
FIG. 4 is an environmental view the window dressing of FIG. 1 securing and protecting a triple lumen catheter, and auxiliary removable securement devices anchoring under the catheter's three pigtail tubings.

Turning to FIG. 4, the dressing 10 is shown applied to a patient's skin to secure and protect a triple lumen catheter C inserted into the patient at an insertion site I. The insertion site I is visible through the opening 22 in the insertion site viewing portion 14 and the catheter hub H is visible through the opening 40 in the anchor member portion 16. The three lumen pigtails L of the catheter C extend from the anchor member portion 16 of the dressing. In FIG. 4, the first and second removable securement devices 68, 79 are disposed on top of the dressing 10 over the folded-over portion of the dressing where the three catheter lumen pigtails L exit from underneath the dressing. The first and second removable securement devices 68, 79 are also disposed underneath the lumen L. The first and second removable securement devices 68, 79 further prevent pulling forces exerted on the catheter lumens L from disturbing the dressing 10.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A window dressing comprising:
a fabric layer having juxtaposed insertion site viewing and anchor member portions;
said fabric layer having an adhesive side and an opposite non-adhesive side;
said insertion site viewing portion being defined by an opening in said fabric layer; and
a transparent film layer having an adhesive skin-adhering side and an opposite non-adhesive side, said film layer being adhered to said fabric layer adhesive side and closing said opening in the fabric layer;
said anchor member portion including a reinforcing structure disposed on said fabric layer and having an adhesive side and an opposite non-adhesive side, said reinforcing structure non-adhesive side being adhered to said fabric layer adhesive side.

2. The window dressing of claim 1, wherein said reinforcing structure includes a central body and a plurality of spaced ribs extending outwardly from the central body.

3. The window dressing of claim 2, wherein said reinforcing structure includes an opening in the central body.

4. The window dressing of claim 2, wherein said reinforcing structure includes a generally circular portion at a terminal end of at least one of said ribs.

5. The window dressing of claim 2, wherein said reinforcing structure is generally symmetric about one of its axes.

6. The window dressing of claim 2, wherein the central body of said reinforcing structure is generally D-shaped.

7. The window dressing of claim 1, including an opening in said anchor member portion of said fabric layer, the opening being generally surrounded by said reinforcing structure.

8. The window dressing of claim 7, wherein said opening in said anchor member portion is smaller in area than said opening in said insertion site viewing portion.

9. The window dressing of claim 1, including a pad member generally circumscribing said viewing portion opening and being adhered to said film layer adhesive side.

10. The window dressing of claim 2, including a pair of side perforation lines, each side perforation line extending inwardly from an edge of said fabric layer and being generally perpendicular to said fabric layer edge.

11. The window dressing of claim 10, including a landmark notch along the fabric layer edge at an end of each side perforation line.

12. The window dressing of claim 1, including a pair of removal perforation lines extending inwardly from an edge of said fabric layer and meeting at a point within said edge.

13. The window dressing of claim 12, including a landmark notch along the fabric layer edge at an end of each removal perforation line.

14. The window dressing of claim 1, including a center cut line extending inwardly from an edge of said fabric layer to said reinforcing structure.

15. The window dressing of claim 1, wherein said dressing is symmetrical about a longitudinal axis.

16. The window dressing of claim 1, further including a first removable securement device comprising:
- a fabric layer having an adhesive side and an opposite non-adhesive side;
- a reinforcing structure having an adhesive side and an opposite non-adhesive side, said non-adhesive side being adhered to said fabric layer adhesive side; and
- a transparent film layer having an adhesive skin-adhering side and an opposite non-adhesive side, said film layer non-adhesive side being adhered to said fabric layer adhesive side;
- wherein said first removable securement device is removably connected to said anchor member portion opposite said insertion site viewing portion by a plurality of frangible lands.

17. The window dressing of claim 16, further including a second removable securement device comprising:
- a fabric layer having an adhesive side and an opposite non-adhesive side;
- a reinforcing structure having an adhesive side and an opposite non-adhesive side, said non-adhesive side being adhered to said fabric layer adhesive side; and
- a transparent film layer having an adhesive skin-adhering side and an opposite non-adhesive side, said film layer non-adhesive side being adhered to said fabric layer adhesive side;
- wherein said second removable securement device is removably connected to said first removable securement device by a plurality of frangible lands.

18. The window dressing of claim 17, wherein said reinforcing structure of said first and second removable securement devices each include a central body and a pair of opposed arms extending from the central body.

19. The window dressing of claim 18, wherein each of said arms includes a bifurcated end.

20. The window dressing of claim 17, wherein said dressing is foldable along a line separating said insertion site viewing portion and said anchor member portion and along a line separating said anchor member portion and said first removable securement device, allowing said dressing to be generally folded in thirds.

* * * * *